United States Patent [19]
Kalbfell et al.

[11] Patent Number: 4,577,043

[45] Date of Patent: Mar. 18, 1986

[54] PROCESS FOR THE PREPARATION OF ALDEHYDES

[75] Inventors: Heinz Kalbfell, Shermbeck; Bernhard Lieder, Bottrop; Herbert Mercamp, Dinslaken, all of Fed. Rep. of Germany

[73] Assignee: Ruhrchemie Aktiengesellschaft, Fed. Rep. of Germany

[21] Appl. No.: 670,357

[22] Filed: Nov. 9, 1984

[30] Foreign Application Priority Data

Nov. 12, 1983 [DE] Fed. Rep. of Germany ....... 3341035

[51] Int. Cl.$^4$ .............................................. C07C 45/50
[52] U.S. Cl. .................................... 568/454; 568/492; 203/17
[58] Field of Search ................... 568/454, 492; 203/17

[56] References Cited

U.S. PATENT DOCUMENTS

| | | | |
|---|---|---|---|
| 3,733,362 | 5/1973 | Biale | 568/454 |
| 4,258,215 | 3/1981 | Dawes | 568/454 |
| 4,306,084 | 12/1981 | Pettit | 568/909 |

FOREIGN PATENT DOCUMENTS

| | | | |
|---|---|---|---|
| 0088955 | 9/1983 | European Pat. Off. | 568/454 |
| 40326 | 11/1973 | Japan | 568/454 |

Primary Examiner—Werren B. Lone
Attorney, Agent, or Firm—Jordan B. Bierman

[57] ABSTRACT

The preparation of aldehydes by the reaction of olefins with carbon monoxide and hydrogen in the presence of water and water-soluble rhodium/phosphine complex compounds as catalysts. The method comprises first cooling the organic part of the liquid phase to 70° to 90° C. in a stripping column by treatment with the carbon monoxide/hydrogen mixture fed into the reactor, further cooling the organic part to 20° to 40° C. by heat exchange with the feed olefin, subsequently relieving the pressure with the consequent formation of waste gas and aqueous and organic phases, and finally separating the phases so as to recover substantially all of the catalyst and the heat of reaction.

9 Claims, 1 Drawing Figure

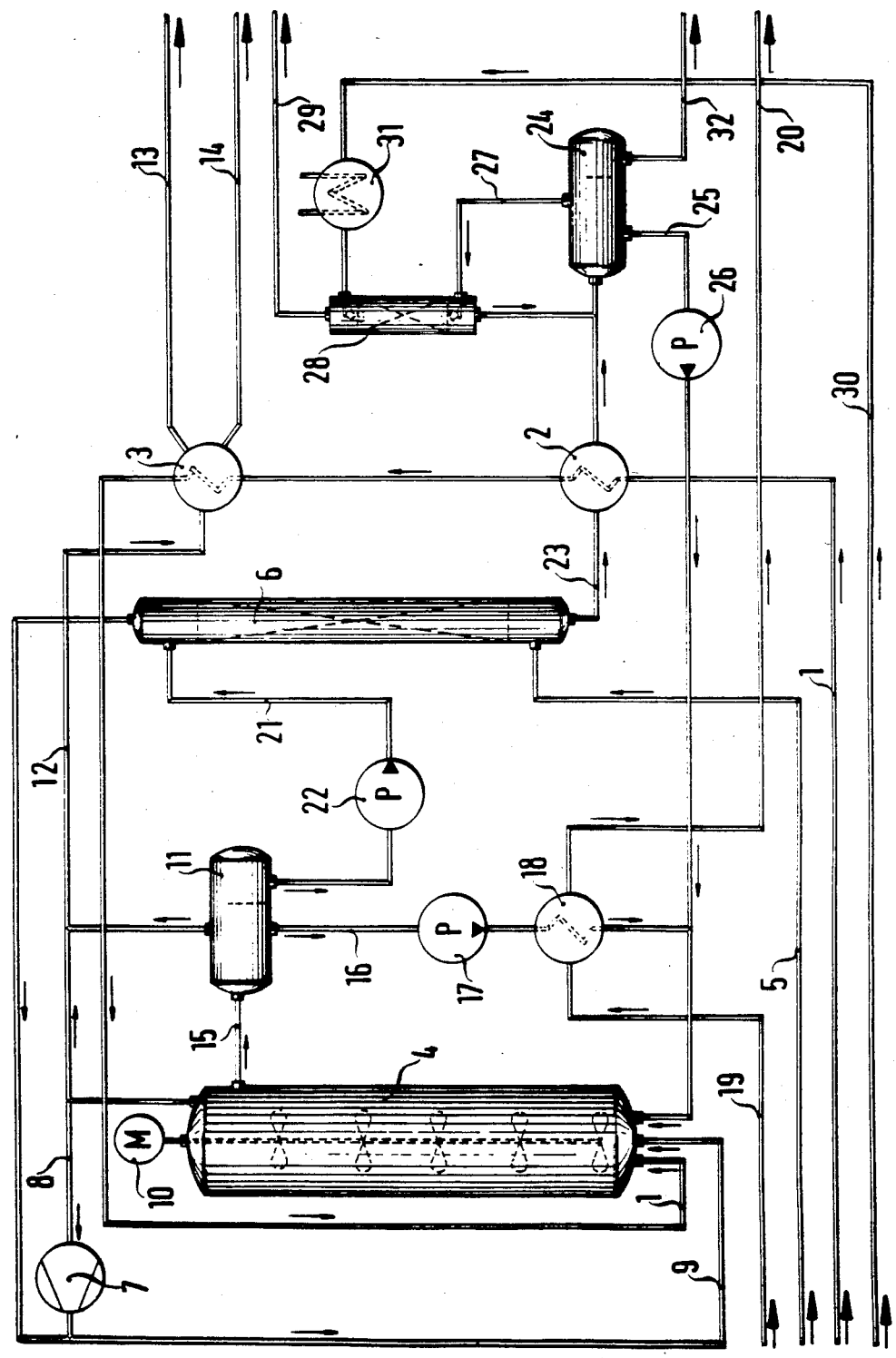

PROCESS FOR THE PREPARATION OF ALDEHYDES

This application claims the priority of German application No. P 33 41 035.6, filed Nov. 12, 1983.

The present invention relates to an improved process for the preparation of aldehydes by the hydroformylation of olefins in the presence of water-soluble rhodium complex catalysts. Such catalysts are described in German Pat. No. 26 27 354. They are rendered water-soluble via the use of trisulfonated triarylphosphines as complex components.

According to a process disclosed in German Published application No. 31 35 127, complexes with metals of the platinum group, which also contain a sulfonated or a carboxylated phosphine, are also used as water-soluble catalysts. The reaction is carried out in a medium consisting of organic and aqueous phases and containing an amphilphilic reagent. A great advantage of using water-soluble hydroformylation catalysts is that they are easy to separate from the reaction product after completion of the reaction; mechanical separation of the aqueous and organic phases (i.e. no distillation) is all that is necessary. Thus, there is no additional energy consumption and high-boiling products are not concentrated in the catalyst phase.

The design of a continuous process for the preparation of aldehydes by the reaction of olefins with carbon monoxide and hydrogen in the presence of water and water-soluble rhodium/phosphine complex compounds is described in German application No. P 32 34 701.4. According to this procedure, the reactants are homogeneously mixed and reacted at temperatures of 90° to 150° C. and pressures of 1 to 300 bar (100 to 30,000 kPAS). The proportion of gaseous components in the liquid phase is adjusted to 5 to 30% by volume based on the mixed phase and the volume ratio of aqueous to organic phase is adjusted to 1:1 to 100:1. The reaction product is obtained, first by the separation of the liquid and gaseous phases, and then by separation of the liquid phase into aqueous and organic parts. Each separation takes place without prior cooling or removal of the heat of reaction.

In practice, the aldehyde reaction product leaving the reactor is fed into a separating vessel, as a mixture of aqueous catalyst solution, unreacted synthesis gas and olefin. There the gas phase—mainly synthesis gas and, depending on their boiling points, olefin, saturated hydrocarbon (formed from and brought in with the olefin), and aldehyde—is separated from the liquid products. The gas phase is recirculated to the reactor and a small amount removed as waste gas. The liquid is separated into a raw organic reaction product and an aqueous phase containing the catalyst, the latter being returned to the reactor. The organic reaction product is then fed into a stripping column and synthesis is passed countercurrent thereto. The synthesis gas absorbs, among other things, the olefin dissolved in the raw product. The raw Oxo product is then distilled and split up into its components.

The economic feasibility of the above process depends on avoiding losses of catalyst, product, and heat. Catalyst losses are, above all, caused by small amounts of catalyst being removed with the raw product. These losses are not economically recoverable due to the low catalyst concentration. Product loss results when the pressure on the product stream, saturated with dissolved synthesis gas, is reduced to atmospheric pressure downstream of the stripping column. The reaction product is partially lost in the waste gas. Finally the heat of reaction is removed from the system with both the waste gas and the removal of the raw product after stripping.

An object of the invention is the development of a hydroformylation process with water-soluble catalysts which avoids the material and energy losses described above.

The instant invention is an improvement in the process for the preparation of aldehydes by the reaction of olefins with carbon monoxide and hydrogen in the presence of water and water-soluble rhodium/phosphine complex catalysts at temperatures of about 90° to about 150° C. and pressures of about 1 to about 300 bar. The process includes dividing the reaction product into liquid and gaseous phases, then separating the liquid phase into first aqueous and first organic parts, each separation being conducted in the absence of prior cooling, and returning the first aqueous part containing the catalyst to the reactor.

The improvement resides in the further treatment of the organic portion. It is cooled, after separation from the aqueous portion, to about 20° to about 40° C., the pressure is then relieved with consequent formation of waste gas which is vented off. The remainder is then separated in a separating vessel into a second organic phase and a second aqueous phase, whereupon the organic phase is distilled to yield an aqueous portion. The aqueous portion and the second aqueous phase are preferably returned to the reactor; however, the catalyst therein may be recovered for utilization elsewhere.

The procedure according to the invention is suitable for converting olefins with 2 to 15 carbon atoms into aldehydes having one more carbon atom. The aldehydes can be converted into the corresponding alcohols by hydrogenation. The coreactant of the olefins is synthesis gas which contains carbon monoxide and hydrogen, preferably in a volume ratio of 1:1. It is possible to vary this ratio in order to achieve certain effects, e.g. to increase the rate of reaction.

The starting materials are reacted at temperatures of about 90° to about 150° C. and pressures of about 1 to about 300 bar in a system consisting of liquid and gaseous phases. The liquid phase consists of two components which are either insoluble or only slightly soluble in each other; (a) the aqueous catalyst solution and (b) the liquid organic reaction product which can also contain a solvent and, in some cases, liquid olefin.

The catalysts used are complexes of rhodium which contain sulfonated or carboxylated phosphines in addition to carbon monoxide and hydrogen. Such phosphines are usually derived from triarylphosphines, wherein aryl is preferably phenyl or naphthyl. It is not necessary that each aryl group have a sulfonic acid or carboxyl group. It has been found that even a single sulfonic acid or carboxyl group on the triaryl phosphine molecule renders the complex sufficiently water-soluble.

The catalyst can be added to the reaction mixture in a preformed state. However, it is also possible to form it in situ. Normally rhodium is added in an amount of about 1 to about 5000 ppm, preferably about 50 to about 800 ppm, based on the aqueous catalyst solution. The sulfonated or carboxylated triarylphosphine must be present in excess of the amount needed to form the rhodium complex. It has been found to be particularly useful to add 1 to 1000 gram moles, preferably 10 to 100 gram moles, of sulfonated or carboxylated phosphine per gram atom of rhodium.

It is important that the aqueous phase be saturated with the gaseous reactants; carbon monoxide, hydrogen and, depending on the reaction conditions and molecular size, gaseous olefin. In order to achieve this, the liquid phase, consisting of aqueous and organic components, and the gaseous phase interface must be maximized. Therefore, the proportion of gaseous components in the liquid phase of the reactants is adjusted to from about 5% to about 30% by volume, based on the mixed phases. The gaseous starting materials are added to the reactor contents under intensive stirring or passed through a distributing apparatus into the liquid reactor contents. Suitable distributing devices include screens or frits. It is also possible to combine stirring and distribution of the gaseous reactants; for example, by the use of an aerating stirrer.

The volume ratio of the aqueous to the organic phase reactants is from about 1:1 to about 100:1, preferably about 10:1 to about 100:1. A sufficient part of the reaction mixture can be removed from the reactor and subjected to phase separation so that, after the aqueous phase has been returned to the reactor, the required volume ratio is established. According to another embodiment of the invention, the phase separation can also be carried out in the reactor in a stabilization zone.

In any case, phase separation is conducted without prior cooling of the reaction mixture. This results in only small amounts of gaseous olefins being dissolved in the components of the reaction mixture which are liquid under the given conditions and, hence, minimizes the amounts of olefins removed with the reaction product. The aqueous part of the liquid phase is returned to the reactor, after replacement, if necessary, of any catalyst losses. The reaction product, i.e. the organic part of the liquid phase, is cooled to temperatures of 20° to 40° C.

According to a preferred embodiment of the invention, the reaction product is cooled by heat exchange with synthesis gas, i.e. the carbon monoxide/hydrogen mixture and/or the feed olefin. Both the synthesis gas and the olefin are subsequently fed into the reactor.

It is particularly useful to cool the reaction product in two stages. In this variant of the instant process, the product is first cooled to about 70° to about 90° C. with carbon monoxide and hydrogen in a stripping column. Cooling then continues in a second stage to about 20° to about 40° C. with feed olefin in a heat exchanger, downstream of the stripping column. The cooled reaction product is then passed into an intermediate depressurization vessel in which the pressure is reduced, usually to about 1 to about 10 bar. By treatment of the raw product with synthesis gas in the stripping column, dissolved gaseous olefin and dissolved saturated hydrocarbon (which is formed from the olefin by hydrogenation or was carried in with the feed olefin) are almost completely removed from the raw product.

It is particularly advantageous that the raw product be cooled in a heat exchanger downstream of the stripping column. This assures that the temperature of the organic phase is below the water saturation point and the dissolved water separates out of the solution. The water can be removed from the organic phase by simple mechanical means without distillation. This is equivalent to a water extraction of the raw product's water-soluble components, which comprise rhodium salts and sulfonated or carboxylated arylphosphines.

The extraction effect can be enhanced by mixing the water fraction of the aldehyde distillation with the raw product before phase separation; this is very effective to minimize catalyst losses. According to a preferred embodiment of the invention, the aqueous phase is returned to the reactor.

Depending on the temperature and the composition of the raw product, the gas formed when the pressure is reduced contains mainly aldehydes. In order to recover these aldehydes as completely as possible, the gas is washed with cold water having a temperature of 5° to 10° C. The wash water is generally fed into the bottom of the stripping column. In this way a considerable reduction in desired product losses is achieved.

BRIEF DESCRIPTION OF THE DRAWING

The drawing is a flow sheet of the process according to the invention.

DETAILED DESCRIPTION OF THE DRAWINGS

Olefin feed gas, introduced via line 1, is heated by the raw product in heat exchanger 2 and by the waste gas in heat exchanger 3, and then fed into reactor 4. Synthesis gas, enriched with olefin in stripping column 6, is fed to reactor 4, in conjunction with recycling gas from compressor 7, via line 9. Recycling catalyst, captured in separator 11 from overflow line 15, is fed back to reactor 4 through line 16, pump 17, and steam generator 18. The aqueous phase obtained from separator 24 is added to the recycling catalyst solution through line 25 and pump 26 after the catalyst emerges from steam generator 18.

Leaving reactor 4, gas is partially recycled through line 8, compressor 7, and line 9. A second portion of the emerging gas joins waste gas from separator 11. Product, catalyst, and additional components leave reactor 4 through overflow line 15.

Separator 11 divides the overflow from line 15 into a waste gas and liquid aqueous and organic portions. The aqueous portion, containing catalyst, is recycled through line 16 as described above. Waste gas passes via line 12 to heat exchanger 3, where it loses heat to the feed olefin. Upon cooling, the waste gas partially condenses into a waste material which leaves the system via line 14. The remaining (uncondensed) waste gas is taken off via line 13 for use elsewhere.

The organic phase emerges from separator 11 and is pumped by pump 22 through line 21 to stripping column 6. Here the organic phase contacts feed synthesis gas entering the stripping column through line 5, where olefins in the organic phase are transferred to the feed synthesis gas.

The remainder of the organic portion (the raw product) leaves stripping column 6 through line 23 and is transferred to heat exchanger 2 where it is used to heat the olefin feed gas. The raw product, together with the aqueous portion emerging from scrubber 28, is then fed into separator 24 after the pressure has been released. Separator 24 divides this into a gas portion, which is vented off through line 27 into scrubber 28; an aqueous portion, recycled to reactor 4 through line 25 as mentioned above; and product, which flows through line 32 for distillation (not shown). The aqueous phase resulting from the distillation enters cooler 31 through line 30 before flowing into scrubber 28. After being scrubbed in scrubber 28, the gaseous portion supplied by line 27 is released as waste gas via line 29.

Line 19 feeds a condensate into steam generator 18 to recapture the heat of reaction from the aqueous phase emerging from separator 11. The steam resulting therefrom is led off by line 20 for use elsewhere.

EXAMPLE

Propylene with a purity of 95% is reacted with synthesis gas ($H_2$:CO molar ratio=1:1) at a pressure of 50 bar and a temperature of 120° C. in the presence of a rhodium triphenylphosphine trisulfonate catalyst.

The reaction product is freed from the gaseous components and split into an aqueous and an organic phase. The organic phase (containing the raw oxo product) is fed, uncooled, to the head of the stripping column. It contains n- and i-butanal. In addition, about 14% by weight propylene, about 9% by weight propane, and 5.3% by weight water are dissolved in the organic phase.

The oxo product is treated in the stripping column, without external heating, with synthesis gas having a temperature, due to compression, of about 80° C. The oxo product temperature cools, from 120° to about 70° C., due to the almost total vaporization of 3 carbon hydrocarbons and a small amount of butanal. Only about 0.1% by weight of 3 carbon hydrocarbons remains dissolved in the raw oxo product.

The raw product leaving the bottom of the stripping column is further cooled to about 40° C. by feed olefin, whereby an aqueous phase containing the dissolved catalyst separates out. This aqueous solution is separated in a downstream separating vessel and returned to the reactor. By this means about 90% by weight of the catalyst is recovered.

The synthesis gas dissolved in the raw product after the stripping column has been passed is released by reduction of the pressure to 3 bar and is cooled with water in a washing column. It is advantageous to use the cooling water to make up the water losses of the catalyst solution.

What we claim is:

1. In a process for the preparation of aldehydes comprising reacting olefins of 2 to 15 carbon atoms with carbon monoxide and hydrogen in a reactor in the presence of water and water-soluble rhodium phosphine complex catalysts at temperatures of from about 90° to 150° C. and pressures from about 1 to about 300 bar; separating said liquid phase into first aqueous and first organic phases without prior cooling; and returning said first aqueous phase containing said catalyst to the reactor;

the improvement which comprises cooling said first organic phase to from about 20° C. to about 40° C.; subsequently relieving the pressure with consequent formation of waste gas; separating said first organic phase into second organic and second aqueous phases; and distilling said second organic phase to yield a third aqueous phase and the aldehyde with one more carbon atom than the olefin.

2. The process of claim 1 wherein said first organic phase is cooled with carbon monoxide and hydrogen and/or said olefin reactant.

3. The process of claim 1 wherein said first organic phase is cooled in a first and second stage.

4. The process of claim 2 wherein said first organic phase is cooled in a first and second stage.

5. The process of claim 3 wherein, in said first stage, said first organic phase is cooled to from about 70° to about 90° C. by said carbon monoxide and hydrogen in a stripping column.

6. The process of claim 3 wherein in said second stage said second organic phase is cooled to from about 20° to about 35° C. by said olefin reactant in a heat exchanger.

7. The process of claim 1 wherein said second aqueous phase is returned to said reactor.

8. The process of claim 5 wherein said waste gas is washed with cold wash water and said wash water is returned to the bottom of the stripping column.

9. The process of claim 1 wherein said catalyst complex is a rhodium/triarylphosphine having at least one sulfonate or carboxylate group thereon and wherein the aryl portion of said complex is phenyl or napthyl; said olefins being selected from olefins having 2 to 15 carbon atoms; said hydrogen and said carbon monoxide are present in a volume ratio of 1:1; gaseous and liquid reactants are in a ratio of 5%–30% by volume; aqueous and organic reactants are in a volume ratio of 1:1 to 100:1; said pressure relieving step reduces the pressure to from about 1 to about 10 bar, and said second and third aqueous phases are returned to said reactor.

* * * * *